United States Patent [19]

Rybka

[11] 4,298,997

[45] Nov. 10, 1981

[54] DEVICE FOR INHIBITING THE FORMATION OF FIBROUS CAPSULAR CONTRACTURES IN SILICONE BREAST IMPLANTS AND METHOD

[76] Inventor: F. James Rybka, 1153 Mariemont Ave., Sacramento, Calif. 95825

[21] Appl. No.: 87,326

[22] Filed: Oct. 23, 1979

[51] Int. Cl.³ .............................................. A61F 1/24
[52] U.S. Cl. ......................................................... 3/36
[58] Field of Search ...................... 3/36; 128/DIG. 21

[56] References Cited

U.S. PATENT DOCUMENTS

| 3,293,663 | 12/1966 | Cronin | 3/36 |
| 3,548,420 | 12/1970 | Spence | 128/DIG. 21 |
| 3,600,718 | 8/1971 | Boone | 128/DIG. 21 |
| 3,616,156 | 10/1971 | Scholl | 128/155 X |
| 3,879,767 | 4/1975 | Stubstad | 128/DIG. 21 |
| 3,914,802 | 10/1975 | Reick | 128/DIG. 21 |

OTHER PUBLICATIONS

Rybka et al., "The Value of Silicone-Sheet Spacers in the Prevention of Spherical Capsular Contractures", paper presented Nov. 10, 1978.

Primary Examiner—Clifford D. Crowder
Attorney, Agent, or Firm—Lothrop & West

[57] ABSTRACT

A circular disc of thin silicone sheet material, such as Silastic, is adhesively attached to an annular band of Dacron felt material, the periphery of the disc and the outer rim of the Dacron felt band being substantially congruent. The combined disc and band are surgically implanted, preferably beneath the chest muscles, with the Dacron felt band against the rib cage. A conventional breast implant having substantially the same diameter as the circular disc is then placed over the disc in register therewith and the incision closed. The arrangement not only gives the surgeon freedom of choice in selecting the implant size and configuration but also reduces the incidence of problems arising from the formation of fibrous capsular contractures in silicone breast implants.

6 Claims, 4 Drawing Figures

U.S. Patent
Nov. 10, 1981
4,298,997
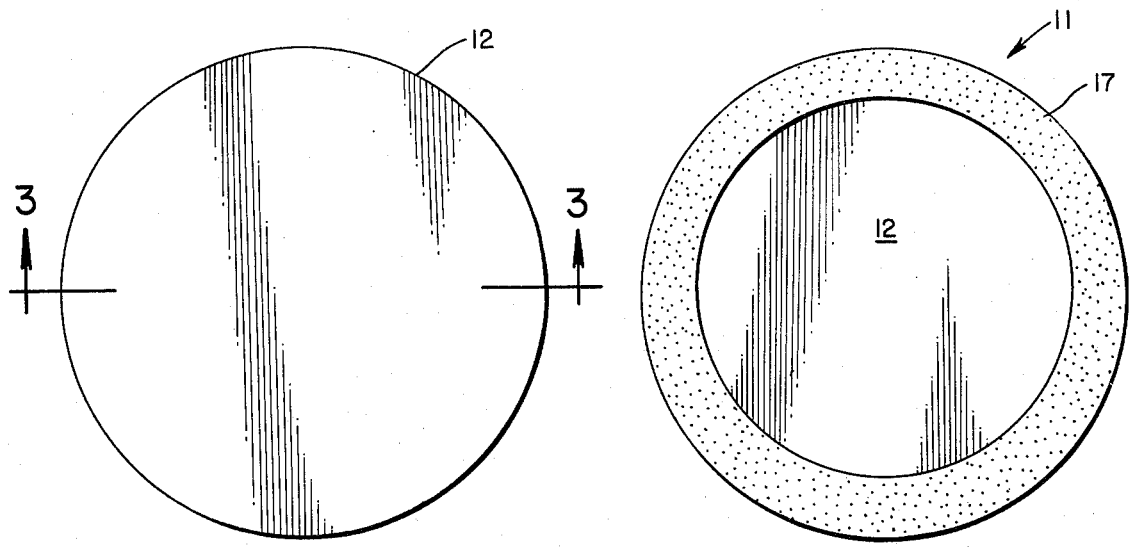
Fig-1
Fig-2
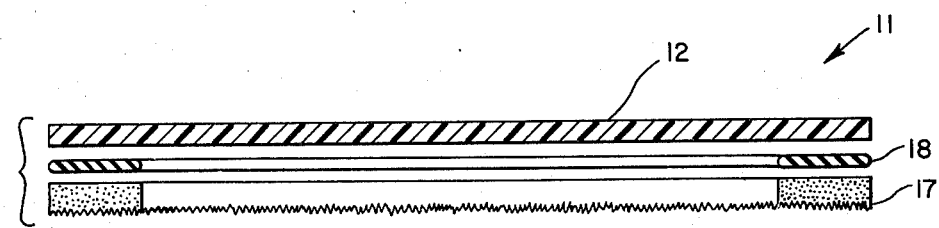
Fig-3
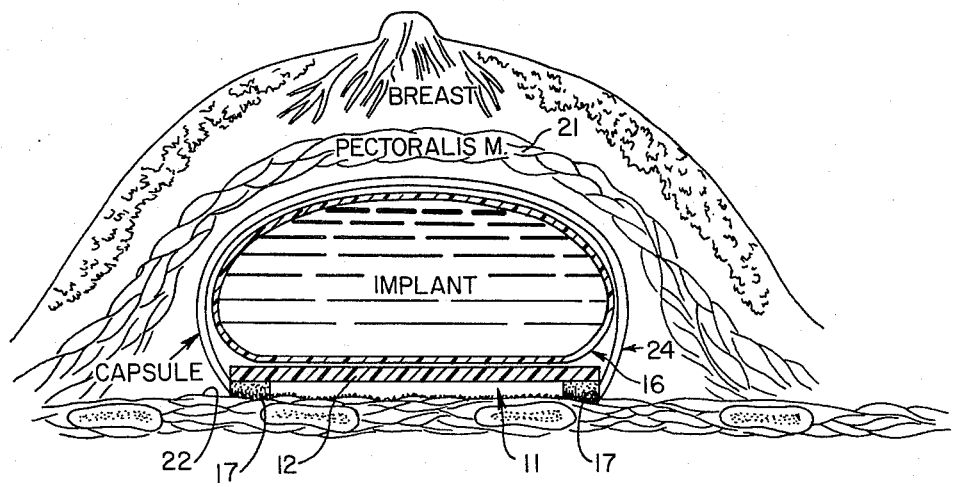
Fig-4

DEVICE FOR INHIBITING THE FORMATION OF FIBROUS CAPSULAR CONTRACTURES IN SILICONE BREAST IMPLANTS AND METHOD

BACKGROUND OF THE INVENTION

Present day surgically implantable human breast prosthesis is often recognized as having originated with the implant disclosed in Cronin U.S. Pat. No. 3,293,663 dated Dec. 27, 1966, in which a silicone gel-filled flexible container approximating the shape of the human breast is provided on the back wall with a layer of porous material, preferably a fabric of polyester fibers commonly sold under the trademark Dacron, into which tissue can grow so as to anchor the prosthesis to the chest wall.

It was subsequently demonstrated, as reported in Williams, J. E.: Experiences with a large series of silastic breast implants. Plast. and Reconstr. Surg. 49:253, 1972, that such anchorage was unnecessary because the fibrous capsule itself is ultimately sufficiently strong to anchor the implant.

In U.S. Pat. No. 3,665,520, dated May 30, 1972, to Perras and Papillon, a surgically implantable breast prosthesis is disclosed in which the back wall of the container is reinforced by a bio-compatible fabric mesh material and the prosthesis is secured to the chest wall of the patient by means of a strip of felt-like material, such as Dacron. The Dacron felt strip is located around the periphery of an axillary prolongation and across the top portion of the back wall of the container.

Somewhat similar means for holding breast prostheses in place is disclosed in Perras U.S. Pat. No. 3,681,787, dated Aug. 8, 1972. In this patent, the container is filled with silicone gel which is more viscous around the outer periphery of the container than in the center of the container, and anchoring is provided by a strip of porous material, such as corrugated Dacron fabric, the strip extending across the top and more than half way around the periphery, but leaving the bottom edge unattached to the chest wall. These prostheses were usually placed prepectorally beneath the mammary gland. Their usage did not appear to become widespread owing, perhaps, to the fact that the ridged back not infrequently became palpable, according to Papillon, J.: Pros and Cons of Subpectoral Implantations; Clinics in Plastic Surgery, Vol. 3, No. 2, April 1976.

The prior art, in other words, relates to implants and means physically attached to the implants for improving their performance.

SUMMARY OF THE INVENTION

The device of the present invention is not a breast implant, nor is it directly attached to a breast implant, although it is in contact therewith.

Instead, it serves as an adjunct to the use of breast implants for reconstruction or augmentation of the human breast and therefore affords the surgeon a choice of implant sizes and configurations.

It is especially suitable for human implantation beneath the chest muscles (pectoralis major) and, more specifically, is constructed and used in such a manner as to prevent, or at least inhibit, the formation of fibrous capsular contractures, one of the most frequent problems currently encountered in connection with silicone breast implants. Breasts which have this complication of fibrous contractures, after surgery may become firm, unnatural in appearance and sometimes painful as a result of the circular cinching caused by the naturally-formed fibrous capsule.

The present device serves as a spacer or barrier which limits the ability of the fibrous capsule to constrict or cinch around the base of the implant beyond a predetermined location. As a result, the tendency of the capsular tissues to contract around the base of a discoid-like implant and thereby urge the implant toward assuming a spherical shape is inhibited.

SHORT DESCRIPTION OF THE DRAWING FIGURES

FIG. 1 is a top plan view;
FIG. 2 is a bottom plan view;
FIG. 3 is an exploded sectional view, to an enlarged scale, the section being taken on the plane indicated by the line 3—3 in FIG. 1; and,
FIG. 4 is a fragmentary median vertical sectional view, showing the shape assumed by the fibrous capsule in conjunction with the present device after the surgical wound has healed.

DETAILED DESCRIPTION OF PREFERRED EMBODIMENT

The device of the present invention, generally designated by the reference numeral II comprises a circular disc 12 of thin, silicone sheeting reinforced with Dacron net lines. The sheet material manufactured by the Dow Corning Corp., (Medical Products Division, Midland, Mich. 48640) having a thickness of 0.007 inch or 0.18 mm. serves very satisfactorily. Preferably, the circular disc 12 is constructed so as to have a diameter approximately one centimeter greater in extent than the diameter of the silicone breast prosthesis 16. Since the construction of and procedures followed in implanting such prostheses are well known and form no direct part of the present invention, the subject of breast implants will not be discussed in detail.

Attached to one side of the circular disc 12 is an annular band 17, or strip, or ring, of Dacron felt material such as that available from Dow Corning Corp., supra. The band 17 is approximately 1.5 cm. in width and the outer margin of the band is congruent with the periphery of the disc 12.

The Dacron felt band 17 is secured to the circular silicone sheet by a layer 18 of silicone adhesive such as Medical Adhesive, Type A, available from Dow Corning Corp., supra.

Based upon a small clinical series as described in Rybka, F. J. et al.: The value of silicone-sheet, Dacron felt spacers in the prevention of spherical contractures, presented at the annual meeting of the American Society of Plastic and Reconstructive Surgeons, Hollywood, Fla., on Nov. 10, 1978, it appears that when the spacer device of the invention 11 is placed over relatively non-rigid body tissues, such as the pectoralis muscle, the force of the contracture exceeds the force of the muscle tending to remain flat. Should such a happening occur, the peripheral edge of the device might be felt by the patient as an annoyance.

Consequently, it is preferred, as appears most clearly in FIG. 4, to locate the device 11 beneath the pectoralis muscle 21 and over the rib cage 22, or chest wall. This greatly reduces the incidence of the type of complication heretofore recited.

With particular reference to FIGS. 3 and 4, it will be noted that the lower or inner surface of the band 17 of Dacron felt, i.e. the portion exposed to the chest wall tissue, tends to be somewhat porous, thus permitting the ingrowth of subjacent tissue after the incision is closed and natural healing takes place.

A firm anchor is thereby provided for the naturally formed fibrous capsule 24 peripherally and loosely enclosing, or encompassing, the implant 16 selected by the surgeon for the particular patient.

At the same time, however, the Dacron felt band 17 presents an effective barrier, or limit, to the cinching or constricting effect around the base of the capsule 24.

It can therefore be seen that not only does the present device afford the surgeon a choice of implants during breast reconstruction or augmentation, but based upon clinical study to date the use of the relatively simple sheet disc and felt ring construction has served to reduce the incidence of problems heretofore encountered as a result of the post-operative formation of fibrous capsular contractures.

It is to be noted that when reference is made herein to the materials identified by the trademarks Silastic and Dacron, it is to be understood that equivalent materials made by other manufacturers are also included.

What is claimed is:

1. Device for inhibiting the formation of fibrous capsular contractures in surgically installed breast implants comprising:
   a. a disc of thin flexible impervious, sheet material, said disc having a shape in plan approximately the same as the shape in plan of the implant; and,
   b. a band of material secured to said disc in congruent marginal edge relation, said band being porous to permit the ingrowth of subjacent tissue from the rib cage and said disc being in unattached engagement with the implant overlying said disc in substantially symmetrical relation in plan as the incision resulting from the surgical installation is closed.

2. A device as in claim 1 in which said disc is circular in plan and said band is annular in plan.

3. A device as in claim 2 in which said disc is of Silastic sheeting having a thickness of about 0.18 mm., and said band is of Dacron felt material approximately 1.5 cm. wide.

4. A device as in claim 3 in which said band is secured to said disc by silicone adhesive.

5. A method for inhibiting the formation of fibrous capsular contractures in breast implants comprising the steps of:
   a. providing a circular disc of thin, flexible, impervious, bio-compatible sheet material and an annular band of porous bio-compatible material secured to the disc in congruent relation;
   b. surgically installing the combined disc and band subpectorally with the band facing the rib cage;
   c. positioning a breast implant above the disc in symmetrical relation;
   d. covering the implant with the pectoral muscle and breast tissue; and,
   e. closing the incision.

6. A method as in claim 5 in which the disc is of sheet Silastic and the band is of Dacron felt.

* * * * *